United States Patent [19]

Grunfield et al.

[11] Patent Number: 5,660,826
[45] Date of Patent: Aug. 26, 1997

[54] THERAPEUTIC SEPSIS TREATMENT USING ANTAGONISTS TO PTHRP

[75] Inventors: Carl Grunfield; Janet Funk, both of San Francisco; Kenneth R. Feingold, San Rafael, all of Calif.

[73] Assignee: The Regents of the University of California, Oakland, Calif.

[21] Appl. No.: 477,348

[22] Filed: Jun. 6, 1995

[51] Int. Cl.$^6$ ............................................. A61K 39/395
[52] U.S. Cl. ..................... 424/145.1; 424/158.1; 514/885
[58] Field of Search ................... 424/145.1, 158.1; 514/885

[56] References Cited

U.S. PATENT DOCUMENTS

| | | | |
|---|---|---|---|
| 4,677,070 | 6/1987 | Larrick et al. | 435/240 |
| 4,771,124 | 9/1988 | Rosenblatt et al. | 530/324 |
| 4,968,669 | 11/1990 | Rosenblatt et al. | 514/12 |
| 5,001,223 | 3/1991 | Rosenblatt et al. | 530/324 |
| 5,055,447 | 10/1991 | Palladino et al. | 514/12 |
| 5,087,561 | 2/1992 | Rosenblatt et al. | 435/7.21 |
| 5,087,562 | 2/1992 | Rosenblatt et al. | 435/7.21 |
| 5,093,233 | 3/1992 | Rosenblatt et al. | 435/7.21 |
| 5,114,843 | 5/1992 | Rosenblatt et al. | 435/7.21 |
| 5,149,779 | 9/1992 | Chorev et al. | 530/317 |
| 5,308,834 | 5/1994 | Scott et al. | 514/12 |
| 5,359,037 | 10/1994 | Wallach et al. | 530/388.22 |
| 5,494,806 | 2/1996 | Segre et al. | 435/69.1 |

FOREIGN PATENT DOCUMENTS

| | | |
|---|---|---|
| 4228089 | 8/1992 | Japan. |

OTHER PUBLICATIONS

Funk, J.L. et al, Endocrinology, vol. 35(1), 1994, pp. 351–358.
Johansson, A.G. et al, Bone & Mineral, 1994, vol. 24, pp. 25–31.
Caruso, A. et al, E.J. Pharmacol., 1991, vol. 198, pp. 85–88.
Chem. Abst., 118, p. 702 (1993). Abstract 118: 100365w.
Baumgartner et al., "Prevention of Gram–Negative Shock and Death in Surgical Patients by Antibody to Endotoxin Core Glycolipid," The Lancet, pp. 59–63 (Jul. 13, 1985).
Bernhagen et al., "MIF is a Pituitary–Derived Cytokine that Potentiates Lethal Endotoxaemia," Nature, 365, pp. 756–759 (Oct. 1993).
Bertini et al., "Adrenalectomy Sensitizes Mice to the Lethal Effects of Interleukin 1 and Tumor Necrosis Factor," J. Exp. Med., 167, pp. 1708–1712 (May 1988).
Beutler et al., "Passive Immunization Against Cachectin/Tumor Necrosis Factor Protects Mice from Lethal Effect of Endotoxin," Science, 229, pp. 869–871 (Aug. 1985).
Cohen et al., "Antibody Titres to a Rough–Mutant Strain of Escerichia Coli in Patients undergoing Allogeneic Bone–Marrow Transplantation," The Lancelet, pp. 8–10 (Jan. 3, 1987).
Doherty et al., "Evidence for IFN–γ as a Mediator of the Lethality of Endotoxin and Tumor Necrosis Factor–α," J. Immunology, 149:5, pp. 1666–1670 (Sep. 1992).
Dunn, David L., "Antibody Immunotherapy of Gram–Negative Bacterial Sepsis in an Immunosuppressed Animal Model," Transplantation, 45:2, pp. 424–429 (Feb. 1988).
Funk et al., "Endotoxin Increases Parathyroid Hormone–related Protein mRNA Levels in Mouse Spleen," J. Clin. Investigation, 92, pp. 2546–2552 (Nov. 1993).
Heinzel, Frederick P., "The Role of IFN–γ in the Pathology of Experimental Endotoxemia," J. Immunol., 145:9, pp. 2920–2924 (Nov. 1990).
Jaspers et al., "Antikörper gegen Lipoid A in der Behandlung des septischen Schocks," Infection, 15, Suppl. 2, pp. S89–S95 (1987).
Law and Marks, "Age–Related Prevalence of Human Serum IgG and IgM Antibody to the Core Glycolipid of Escherichia coli strain J5, as Measured by Elisa," J. Infect. Diseases, 151:6, pp. 988–994 (Jun. 1985).
Martin et al., "Parathyroid Hormone–Related Protein: Biochemistry and Molecular Biology," Critical Reviews in Biochemistry and Molecular Biology, 26:3/4, pp. 377–395 (1991).
Ohlsson et al., "Interleukin–1 Receptor Antagonist Reduces Mortality from Endotoxin Shock," Nature, 348, pp. 550–552 (Dec. 1990).
Stewart and Broadus, "Clinical Review 16: Parathyroid Hormone–Related Proteins: Coming of Age in the 1990s," Journal of Clinical Endocrinology and Metabolism, 71:6, pp. 1410–1414 (1990).
Tracey et al., "Anti–cachectin/TNF Monoclonal Antibodies Prevent Septic Shock During Lethal Bacteraemia," Nature, 330, pp. 662–664 (Dec. 1987).
Dinarello, C. A. et al. 1993. "Anticytokine Strategies in the Treatment of the Systemic Inflammatory Response Syndrome." Journal of the American Medical Association 269:1829–1835.

*Primary Examiner*—James C. Housel
*Assistant Examiner*—Ginny Allen Portner
*Attorney, Agent, or Firm*—Majestic, Parsons, Siebert & Hsue

[57] ABSTRACT

Methods and compositions are provided for the treatment or prophylaxis of systematic inflammatory response syndrome by administering an antagonist to parathyroid hormone-related protein, such as antibodies to PTHrP.

9 Claims, 1 Drawing Sheet

THERAPEUTIC SEPSIS TREATMENT USING ANTAGONISTS TO PTHRP

This invention was made with Government support under Grant No. DK 47846 awarded by the National Institutes of Health and funds from the Research Service of the Department of Veterans' Affairs. The Government has certain rights in this invention.

FIELD OF THE INVENTION

This invention relates generally to a method of treating severe inflammatory conditions, such as systemic inflammatory response syndrome, which results from e.g., sepsis, and more particularly to administering an antagonist to parathyroid hormone-related protein.

BACKGROUND OF THE INVENTION

Systematic inflammatory response syndrome is the designation recently established by a group of researchers to describe related conditions resulting from, for example, sepsis, pancreatitis, multiple trauma such as injury to the brain, and tissue injury, such as laceration of the musculature, brain surgery, hemorrhagic shock, and immune-mediated organ injuries. A variety of different approaches have been suggested for treating inflammatory conditions or septic (endotoxin) shock.

U.S. Pat. No. 5,308,834, issued May 3, 1994, inventors Scott et al., discloses a method said to prevent endotoxemia in a subject by administering an amount of a leukocyte protein (BPI) effective to prevent endotoxemia in the subject.

Among the therapeutic approaches, antibodies directed against endotoxin or its components have been evaluated for their utility in immunotherapy of sepsis. Murine and human monoclonal antibodies directed against the core lipopolysaccharide of the endotoxin have been reported to exert protection during Gram-negative bacterial sepsis in animals. Dunn, *Transplantation*, 45, 424–429 (1988). Antibodies directed against lipid A also have been reported to have a protective effect in humans. Jaspers et al., *Infection*, 15 Supp. 2, S89–95 (1987). Antibodies to the J5 mutant of *E. coli* are reported to be protective against septic shock in animals and humans. Cohen et al., *Lancet*, 1, 8–11 (1987); Law and Marks, *J. Infect. Dis.*, 151, 988–994 (1985). Antibodies to endotoxin core glycolipid have been reported to prevent the serious consequences of Gram-negative infections in surgical patients. Baumgartner et al., *Lancet*, 2, 59–63 (1985). In addition, human monoclonal antibodies to *P. aeruzinosa* exotoxin A and exoenzyme S have been described as useful for this purpose. U.S. Pat. No. 4,677,070, issued Jun. 30, 1987.

Many of the toxic effects of endotoxin are mediated by cytokines, hormones, and other small molecules. Blockade of these various mediators has been used to treat sepsis. In animal models prior administration of antibody directed against TNF was reported to protect from the lethal effects of endotoxin. Beutler et al., *Science*, 229, 869 (1985). Also, antibody blockade experiments were reported showing that various cytokines, such as TNF, are mediators of the lethal effects of endotoxin. Tracey et al., *Nature*, 330, 662 (1987); Ohlsson et al., *Nature*, 348, 550 (1990); Heinzel, *J. Immunol.*, 145, 2920 (1990); Doherty et al., *J. Immunol.*, 149, 1666 (1992); Bernhagen et al., *Nature*, 365, 756 (1993). More recently, either polyclonal or monoclonal antibodies to a human tumor necrosis factor binding protein (TBP-I) have been described for application in modulating the response to tumor necrosis factor, such as to suppress deleterious effects of this cytokine. U.S. Pat. No. 5,359,037, issued Oct. 25, 1994, inventors Wallach et al.

The treatment of endotoxemia or sepsis by passive immunization with endotoxin neutralizing antibodies or cytokine antibodies is a relatively new approach. However, to date many of the approaches suggested for sepsis treatment have not proven very efficacious. It is likely that treatment for septicemia in the future will combine a plurality of approaches, in view of the large cascade of pro-inflammatory cytokines unleashed during the host response to infection.

Since morbidity and mortality associated with endotoxemia remains high, new adjunct therapies are being sought because septicemia remains the leading case of death in intensive care units in the United States.

SUMMARY OF THE INVENTION

In one aspect of the present invention, a method of treating a patient for a systemic inflammatory response syndrome comprises administering a pharmaceutically effective amount of a parathyroid hormone-related protein blocker to the patient. Thus, patients are treated for a systemic inflammatory response syndrome resulting from conditions such as sepsis.

Comparison between groups of inventively treated and control animals showed that the inventive treatment provided a significant protective effect from an induced inflammatory response syndrome mortality, although the treatment delayed but, ultimately, did not prevent death. Thus, therapy in accordance with the invention preferably includes an additional (or a plurality of) approach(es) to block the cascade of pro-inflammatory cytokines.

DETAILED DESCRIPTION OF THE PREFERRED EMBODIMENTS

Figure 1:
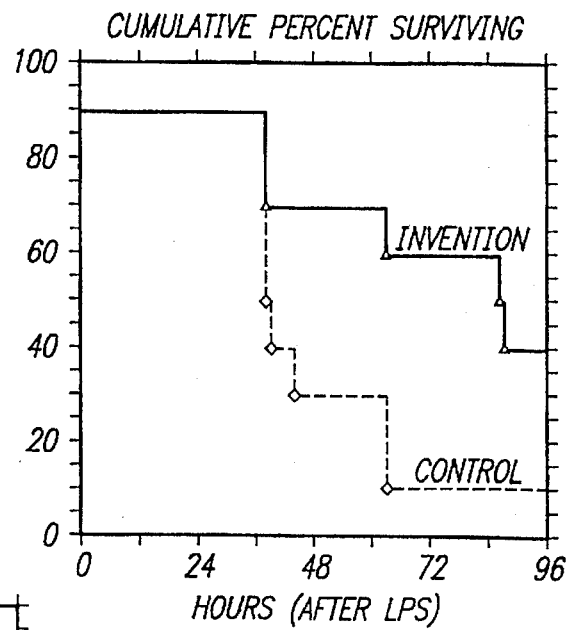
FIG. 1 graphically illustrates the effect of goat anti-serum directed against a 34 amino acid fragment of PTHrP on mice that have been administered lethal doses of endotoxin. The dashed line represents similarly treated mice to which were administered naive goat serum as control antibody.

Parathyroid hormone-related protein (PTHrP) was isolated and identified in the late 1980s. The amino acid sequence of human, rat, mouse, and chicken PTHrPs are known to the art and are discussed by Martin et al., *Crit. Rev. Biochem. Mol. Biol.*, 26, pp. 377–395 (1991). PTHrP and PTH, one of the primary hormones responsible for calcium homeostasis, appear to be derived from a common ancestral gene. However, PTHrP is more highly conserved than PTH. Although PTHrP shares little primary sequence homology with PTH, N-terminal segments of both peptides bind with similar affinity to PTH receptors present in kidney and bone, the classic target tissues for PTH action. The 1-13 region of PTHrP is 70% homologous with the corresponding region of PTH. The 14-34 region of PTHrP shares no homology with the 14-34 region of PTH, although there is apparently a similar tertiary, 3-dimensional or steric homology between PTHrP and PTH in the 14-34 region.

In malignancy, high circulating levels of tumor-derived PTHrP cause hypercalcemia by inappropriately stimulating bone resorption and renal calcium reabsorption via interaction with PTH/PTHrP receptors at these sites. In contrast, PTHrP is barely detectable in the circulation of normal individuals. However, PTHrP is widely expressed in normal tissues, thus leading to the hypothesis that this peptide normally acts at its site of production in a paracrine or autocrine fashion. Consistent with this hypothesis, the recently cloned PTH/PTHrP receptor, in addition to being present in bone and kidney, has also been found to be expressed in many of the same tissues that produce PTHrP.

While PTHrP has been defined by its relation to PTH, a hormone that follows the normal endocrine paradigm of localized production and distant action, we believe that PTHrP may in fact act more like a cytokine than a classic hormone and that its effect on bone and calcium metabolism may be but one of many important biological functions. We have found a therapeutic role for antibodies to PTHrP in significantly protecting from sepsis lethality.

Although the precise cause of death from sepsis is unknown, hypotension is a hallmark of lethal endotoxemia. Alterations in vascular hemodynamics are also thought to contribute to the multisystem organ failure that accompanies sepsis. In septic shock, systemic vascular resistance is low due to vasodilation and, although cardiac output increases in an attempt to maintain blood pressure, cardiac contractility is decreased.

The present invention is the therapeutic use of a PTHrP antagonist. By "PTHrP antagonist" is meant to include compounds that block PTHrP activity at the PTHrP receptor, and which include PTH or PTHrP fragments (e.g. fragments with the 3-34 or 7-34 amino acid residues of PTH or PTHrP and fragments in which one or more amino acid residues have been replaced with analogues), monoclonal or polyclonal antibodies to PTHrP, and non-peptide analogs that can be designed to mimic the effects of peptides such as the 3-34 or 7-34 amino acid residue fragments. The polyclonal or monoclonal antibodies may be raised in rabbits, mice, or other animals or tissue cultured cells or can be products of cells of human origin. They may also be produced of recombinant DNA technology either in a form identical to that of the native antibody or as chimeric molecules, constructed by recombination of antibody molecules of man and animal origins or in other forms chosen to make the antibodies most suitable for use in therapy. The replacement of amino acid residues and the amide forms (at the C terminus) for analogues are known. Illustrative suitable analogues in accordance with the invention are where Nle is at the 8 and 18 positions and Tyr at the 34 of an amidated 3-34 parathyroid (bovine or human) fragment, where Tyr is at the 34 position of an amidated 7-34 (bovine) fragment, the amidated 7-34 fragment of PTHrP (human), where Leu is at 11 and D-Trp is at 12 of an amidated 7-34 PTHrP (human) fragment, where Asn is at 10, Leu at 11, and D-Trp at 12 of the 7-34 PTHrP fragment, and where D-Trp is at 12 and Tyr at 34 of an amidated 7-34 PTHrP (bovine) fragment.

In accordance with the inventive method, the PTHrP antagonist is administered prophylactically or therapeutically (that is, before, simultaneously with, or after) infection has set in. For example, when administering prophylactically, one particularly considers patients at risk such as those suffering from severe thermal burns, receiving immunosuppressive therapy, undergoing extensive surgical procedures, organ transplantation, or suffering other serious injuries or disease.

The PTHrP antagonist as therapeutic agent is administered to the patient by any suitable technique, preferably parenteral and, if desired intralesional. The specific method of administration will depend, e.g., on whether the administration is therapeutic or prophylactic. Thus, in view of the therapeutic urgency usually attending shock, the PTHrP antagonist may be intravenously infused at the same time as solutions used for initial volume expansion. Continuous infusion is preferred for administering peptides while bolus infusion may be used when administering antibodies. Prophylaxis is generally accomplished, e.g., by intramuscular or subcutaneous administration or other parenteral administration, including intraarterial and intraperitoneal administration, preferably intravenous or intraperitoneal.

The PTHrP antagonist compositions to be used in the inventive therapy will be formulated and dosed in a fashion consistent with good medical practice taking into account the clinical condition of the individual patient, the cause of the septic shock, whether the PTHrP antagonist is used for therapy of shock or prophylaxis of incipient septic shock, the site of delivery of the PTHrP antagonist, the method of administration, the scheduling of administration, and other factors known to practitioners. The "effective amount" for purposes herein is thus determined by such considerations.

As a general proposition, the total pharmaceutically effective amount of the PTHrP antagonist administered parenterally per dose will be in the range of approximately 1 µg/kg to 10 mg/kg of patient body weight once per day, although, as noted above, this will be subject to a great deal of therapeutic discretion. As earlier noted, where the PTHrP antagonist is a peptide or an analog of a peptide, then administration is preferably by continuous infusion. The key factor is selecting an appropriate dose and scheduling is the result obtained. Relatively higher doses may be needed initially for the treatment of profound shock, i.e., for patients in acute renal failure or respiratory distress, or having severely depressed blood pressure (mean arterial pressure below about 60 mm Hg).

For parental administration, the PTHrP antagonist is formulated generally by mixing it at the desired degree of purity, in a unit dosage injectable form (solution, suspension, or emulsion), with a physiologically acceptable carrier, i.e., one that is non-toxic to recipients at the dosages and concentrations employed. Preferably the carrier is a parenteral carrier. Examples of such carrier vehicles include water, saline, Ringer's solution, dextrose solution, and 5% human serum albumin. Non-aqueous vehicles such as fixed oils and ethyl oleate are also useful herein, as well as liposomes. Generally, the carrier can contain minor amounts of additives such as substances that enhance isotonicity and chemical stability, e.g., buffers and preservatives, as well as low molecular weight (less than about 10 residues) polypeptides, proteins, amino acids, carbohydrates including glucose or dextrans, chelating agents such as EDTA, or other excipients. The PTHrP antagonist is typically formulated in such vehicles at a concentration of about 0.1 mg/ml to 100 mg/ml at pH range 4 to 7.

A PTHrP antagonist for use in therapeutic administration must be sterile. This is readily accomplished by sterile filtration through (0.2 micron) membranes. The PTHrP antagonist selected ordinarily will be stored as an aqueous solution or can be lyophilized.

PTHrP antagonist therapy or prophylaxis is suitably combined (indeed, preferably combined) with other proposed or conventional therapies or prophylactic treatment for septic shock. For example, for treatment of burns, the PTHrP antagonist therapy may be delivered by separate means, simultaneously with and by the same administration route as other substances such as antibiotics, or anti-microbial agents that inhibit bacterial colonization of the burn wound surface. Other therapies that can be combined with PTHrP antagonist therapy include other cytokine antagonists, such as anti-TNF, antagonists of IL-1, and inhibitors of platelet activating factor. For example, Ohlsson et al., supra, have reported that a specific interleukin-1 receptor agonist reduces mortality from endotoxin shock while Doherty et al. and Heinzel, supra, discuss the use of anti-IFN-γ to reduce mortality from endotoxic shock. Further, the inventive method can be practiced in conjunction with primary therapeutic agents, for example, potent anti-microbial agents such as aminoglycosides (such as amikacin, tobramycin netilmicin, and gentamicin), cephalosporin, related beta lactam agents such as moxalactam, carbopenems such as imipenem, monobactam agents such as aztreonam, ampicillin and broad-spectrum penicillins (e.g., penicillinase-resistant penicillins, ureidopenicillins, or anti-pseudomonal penicillins).

It is known that the pathophysiologic consequences of Gram-negative sepsis are primarily mediated by the release of bacterial endotoxin. Thus, endotoxin treatment of mice is used as an experimental model of gram negative sepsis. For example, in U.S. Pat. No. 5,308,834, a group of rats was given a single, bolus injection of 0.5 mg/kg body weight bacterial endotoxin in studying the effects of leukocyte protein ("BPI"), with the results said to support the use of BPI to reduce mortality due to sepsis. Similarly, U.S. Pat. No. 5,055,447, issued Oct. 8, 1991, inventors Palladino et al., used mice as a model in endotoxin studies.

We have also used the injection of a near-lethal dose of endotoxin as a model for septic shock (a state of profound hypotension and multi-organ failure resulting from a systemic inflammatory response to overwhelming infection by Gram-negative or other bacteria) in mice and rats as models of sepsis.

Thus, mice were passively immunized with antibody generated against the 1-34 fragment of PTHrP, which is a peptide fragment that is active at the PTH/PTHrP receptor, prior to the administration of a lethal dose of endotoxin. Anti-PTHrP antibodies were raised both in goats and in rabbits by immunizing the animals with synthetic human PTHrP.

The immunoglobulin fraction of immune sera (PTHrP antibody) or naive sera (control antibody) was partially purified by ammonium sulfate precipitation (33% saturation) using previously described techniques to avoid the introduction of endotoxin contamination. The endotoxin content of PTHrP and control antibody solutions, determined by Limulus assay (sensitivity, 10 pg/ml), was below the levels required to alter sensitivity to subsequent (6 h) LPS challenge in mice.

Figure 2:
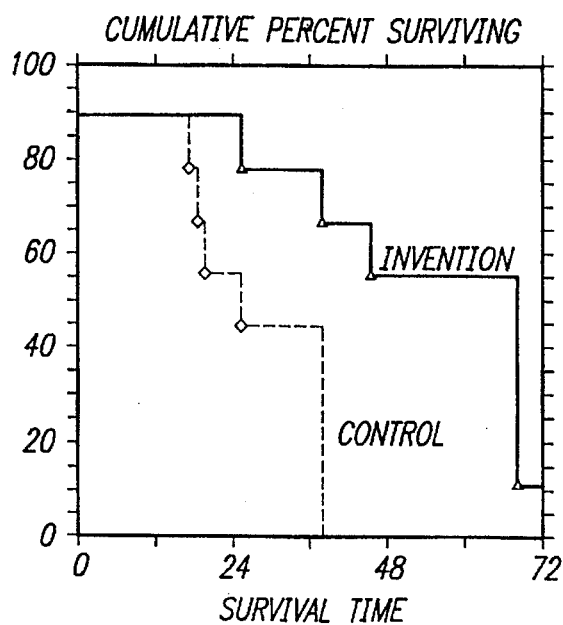
FIG. 2 is similar to FIG. 1, but illustrates rabbit anti-serum administrations.

Administration of goat PTHrP antibody 6 h prior to the injection of the endotoxin ("LPS") significantly protected mice from death when compared to the mortality rate ($LD_{90}$) seen in mice treated with goat control antibody ($p<0.03$ by log rank analysis of Kaplan Meier curves) (FIG. 1). The protective effect of PTHrP antibody was confirmed in other studies utilizing antiserum raised in a different species (rabbit) against the same antigen. Passive immunization of mice with rabbit PTHrP antibody similarly protected mice from death caused by administration of LPS when compared to control mice treated with rabbit control antibody ($p<0.004$ by log rank test of Kaplan Meier survival curves) (FIG. 2). The degree of protection from LPS lethality seen here with passive immunization against PTHrP is similar to that reported for passive immunization of mice against TNF, a major mediator of sepsis.

Figure 3:
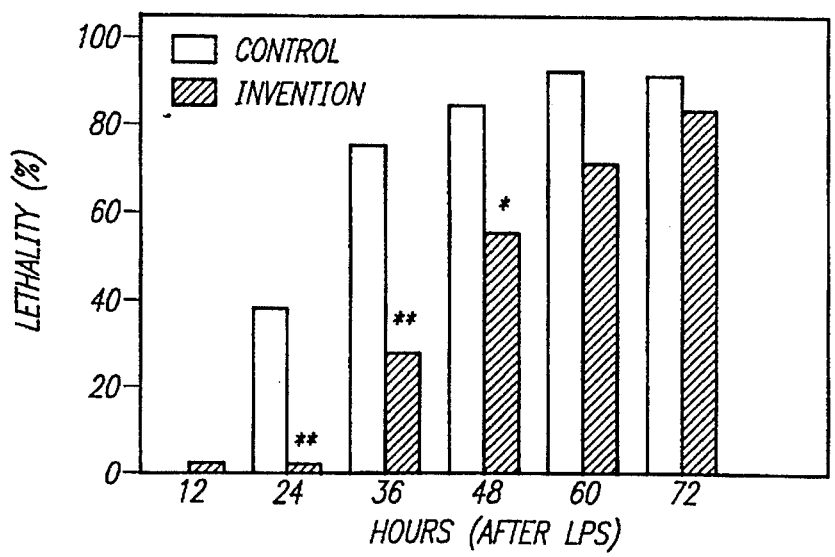
FIG. 3 is similar to FIG. 2, but lethality data from five separate experiments were combined for analysis.

Comparison of survival curves for PTHrP antibody- versus control antibody-treated groups showed that PTHrP antibody provided a significant protective effect from LPS-induced death over the 3 to 4 day course of the experiments (FIGS. 1 and 2), although the relative survival rates at the end of the observation periods were no different (as determined by Fisher's exact test). Thus, the PTHrP antibodies administered delayed but, ultimately, did not prevent death. Compilation of data from multiple experiments (n=90 mice) examining the ability of rabbit PTHrP antibody to protect from LPS-induced death confirms this conclusion. While overall survival was improved by pretreatment with rabbit PTHrP antibody ($p<0.00005$ by log rank analysis), comparison of lethality rates at 12 h intervals following LPS administration only showed a significant protective effect during the first 48 hours following LPS administration (FIG. 3).

In summary, these data show that PTHrP is effective in mediating at least some of the toxic effects of endotoxin, as evidenced by the ability of antibody directed against PTHrP to delay LPS-induced death.

Antibody blockade experiments, similar to those presented here, have previously shown that numerous other cytokines, such as TNF, IL-1, macrophage inhibitory factor (MIF) and IFN-γ, are also mediators of the lethal effects of endotoxin. The fact that passive immunization against PTHrP delays, but does not ultimately prevent, lethality from LPS is consistent with the hypothesis that PTHrP is one member of a larger cascade of pro-inflammatory cytokines that is unleashed during the host response to infection, and therapy in accordance with the invention will preferably include one or more approaches to block the cascade.

Turning to FIG. 1 and FIG. 2, the data shows the effect of goat (FIG. 1) or rabbit (FIG. 2) antiserum directed against PTHrP on LPS-induced lethality in mice. The details of the data are summarized by FIGS. 1–3 are given by Examples 1–3.

EXAMPLE 1

Male C57BL/6 5–6 week old mice (n=9/group) were injected intraperitoneally (ip) with 200 μl ammonium sulfate-precipitated goat antisera (PTHrP antibody, open triangle) (titre 1:8,000 by ELISA; LPS, undetectable) or ammonium sulfate-precipitated naive goat sera (control antibody, open circle) (LPS, undetectable) 6 h prior to the administration of 700 μg 055:B5 LPS diluted in apyrogenic 0.9% saline. Animals, given access to chow and water ad libitum, were monitored for lethality for 96 h after LPS treatment. Statistical analysis of the Kaplan Meier survival curves for the two groups (Statistica 4.1, StatSoft) using either a log rank test which gives equal weight to all points or the Peto & Peto Wilcoxon Test which weights earlier time points more heavily showed that pretreatment with PTHrP antibody protected mice from LPS-induced lethality ($p<0.030$ and $p<0.031$, respectively).

EXAMPLE 2

Mice (n=8/group) were injected with 100 μl ammonium sulfate precipitated rabbit antisera (open triangle) (titre 1:16,000; 6-fold concentrated by volume; 100 pg LPS/100 μl) or ammonium sulfate-precipitated naive rabbit serum (open circle) (5-fold concentrated by volume; 165 pg LPS/ 100 μl) 6 h prior to the administration of 700 μg LPS ip. Animals were then monitored as in (A). Statistical analysis of the Kaplan Meier survival curves for the two groups showed that pretreatment with PTHrP antibody protected mice from LPS-induced death ($p<0.004$ by log rank test; $p<0.003$ by Peto & Peto Wilcoxon Test). Results are representative of 5 separate experiments.

EXAMPLE 3

Turning to FIG. 3, the data shows the effect of rabbit antisera directed against PTHrP on LPS-induced lethality. Lethality data from 5 separate experiments, performed as described in FIGS. 1 and 2, were combined for analysis. For a given experiment, C57BL/6 mice received an equal volume (100–500 µl) of PTHrP or control rabbit antibody. Since PTHrP antibody was ammonium sulfate-precipitated from different rabbit bleeds for different experiments, the volume of ammonium sulfate precipitated-PTHrP antibody used was adjusted so that an equivalent titer of PTHrP antibody was administered in all experiments (e.g. 100 µl of 1:16,000; 300 µl of 1:5,500; or 500 µl of 1:3,200). Control and PTHrP antibody solutions were matched for fold-concentration (4–6-fold concentrated relative to serum) and contained less than 165 pg LPS/volume injected. Six hours after antibody administration, mice from both treatment groups were injected with an equal amount of LPS (650–800 µg LPS, corresponding to an $LD \geq 80$ at $t=48$ h in control-antibody treated mice). Statistical analysis of Kaplan Meier survival curves (not shown here) for PTHrP (n=43) and control (n=47) antibody-treated groups showed that pretreatment with PTHrP antibody protected mice from LPS-induced death ($p<0.00005$ by log rank analysis and $p<0.000001$ by Peto & Peto Wilcoxon test). Comparison of lethality at 12 h intervals after LPS administration (from $t=0-96$ h) using Fisher's exact test (Instat 2.01, GraphPad Software, San Diego, Calif.) showed that PTHrP antibody significantly protected animals from LPS-induced lethality when compared to control antibody-treated mice at the early time points shown.

It is to be understood that while the invention has been described above in conjunction with preferred specific embodiments, the description and examples are intended to illustrate and not limit the scope of the invention, which is defined by the scope of the appended claims.

It is claimed:

1. A method comprising:

administering to a patient suffering from risk of systemic inflammatory response syndrome (SIRS) a pharmaceutically effective amount of antibodies to parathyroid hormone related protein (PTHrP), the amount administered being effective in reducing or delaying at least some of the toxic effects of endotoxin or cytokine.

2. The method as in claim 1 wherein the pharmaceutically effective amount is about 1 µg/kg to 10 mg/kg of patient body weight.

3. The method as in claim 1 wherein the administration is by continuous infusion or bolus infusion.

4. The method as in claim 1 wherein the administration is to a patient having a microbial infection but not yet showing symptoms of septic shock.

5. The method as in claim 1 wherein the antibodies to PTHrP are administered with an anti-microbial agent.

6. The method as in claim 1 wherein the antibodies to PTHrP are monoclonal antibodies.

7. The method as in claim 1 wherein the SIRS is septic shock.

8. The method as in claim 7 wherein the administering is in conjunction with an additional cytokine antagonist.

9. The method as in claim 7 wherein the additional cytokine antagonist is an anti-TNF agent, an IL-1 antagonist, or an inhibitor of platelet activating factor.

* * * * *

UNITED STATES PATENT AND TRADEMARK OFFICE
CERTIFICATE OF CORRECTION

PATENT NO. : 5,660,826
DATED : August 26, 1997
INVENTOR(S) : Grunfeld et al.

It is certified that error appears in the above-indentified patent and that said Letters Patent is hereby corrected as shown below:

On the Title Page, items [19] and [75]:
   replace "Grunfield" with:

--Grunfeld--

Signed and Sealed this

Third Day of March, 1998

Attest:

Attesting Officer

BRUCE LEHMAN

Commissioner of Patents and Trademarks